United States Patent [19]

Barker

[11] Patent Number: 5,009,338

[45] Date of Patent: Apr. 23, 1991

[54] INDICATOR CAP FOR A MEDICINE BOTTLE

[75] Inventor: Allan Barker, Boulder, Colo.

[73] Assignee: Senetics Corporation, Boulder, Colo.

[21] Appl. No.: 306,485

[22] Filed: Feb. 3, 1989

[51] Int. Cl.$^5$ ............................................. B65D 51/24
[52] U.S. Cl. ..................................... 215/230; 116/308; 206/534
[58] Field of Search ................ 215/222, 230; 206/534; 116/308, 309, 311, 312

[56] References Cited

U.S. PATENT DOCUMENTS

| | | | |
|---|---|---|---|
| 3,151,599 | 10/1964 | Livingston | 215/230 X |
| 3,921,568 | 11/1975 | Fish | 116/308 |
| 4,011,829 | 3/1977 | Wachsmann et al. | 206/534 X |
| 4,432,300 | 2/1984 | Lyss | 206/534 X |
| 4,528,933 | 7/1985 | Allen | 116/312 X |
| 4,646,936 | 3/1987 | Frazier et al. | 206/534 X |
| 4,666,051 | 5/1987 | Trick | 215/230 |
| 4,749,093 | 6/1988 | Trick | 215/230 X |
| 4,753,189 | 6/1988 | Mastman et al. | 206/534 X |
| 4,782,966 | 11/1988 | Thackrey | 215/230 |

FOREIGN PATENT DOCUMENTS 0230323 7/1987 European Pat. Off. .

*Primary Examiner*—Stephen Marcus
*Attorney, Agent, or Firm*—Greenlee and Associates

[57] ABSTRACT

Disclosed is an indicator cap for indicating each time a bottle is opened and re-closed having an outer cover shaped in the manner of a conventional bottle cap with a window in the top piece of the cap. The cap is designed to be attached to the sealing cap of the container such that some motion can occur between the two caps during opening and closing of the container, and this lost motion drive is used to advance the indicator. Underneath the window, and within the body of the device, is an indicator wheel having numbers, days, times, etc. engraved or printed thereon which are visible through the window to indicate the next time a dose of the medication should be taken. The indicator wheel contains a pawl formed therein or attached thereto that engages a set of teeth, formed in the underside of the top piece of the outer cover, only when the device is being opened. This engagement causes the indicator wheel to move to the next index location each time the cap is opened. Underneath the indicator wheel, and attached to the outer cover is a snap cover which contains a pawl formed therein or attached thereto. The pawl engages a set of teeth on the indicator wheel to prevent the indicator wheel from moving with respect to the ratchet when the device is being closed. The pawls on the two wheels, and the teeth formed opposite the pawls are designed such that the index wheel moves to a new location upon opening the cap, and is kept in that location when the cap is closed, allowing the window in the top piece to uncover the next indicator as the device is closed. Both pawls are formed or attached such that space is provided for the pawl to move out of the way when being moved in a direction where the teeth are disengaged. The pawl moves away from the teeth as the teeth slide over the pawl, and as the movement is completed, the pawl makes an audible sound as it snaps back into place. Thus, the device makes a sound when it has been opened a sufficient amount for the index to move to the next location, and it also makes a sound when is has been closed sufficiently to re-cock the mechanism for the next cycle. The device also has an extension plug that attaches between the snap cover and the sealing cap to allow the indicator cap to be attached to a sealing cap that is larger than the outer cover. Also disclosed in an alternative embodiment wherein the snap cover and the sealing cap are formed as a single unit. A second alternative embodiment is disclosed wherein the lost motion drive is formed by a retainer disc, a separate ratchet, and a bottom piece for attachment to the sealing cap of the bottle.

10 Claims, 8 Drawing Sheets

INDICATOR CAP FOR A MEDICINE BOTTLE

BACKGROUND OF THE INVENTION

The present invention relates to closure members for containers, bottles and the like, and, more particularly, to closure members having indicator means to indicate the number of times the container has been opened.

Present medical drugs have a predetermined therapeutic range in which the effects of taking the drug are beneficial. Under utilization of a drug may endanger the user with the drug's side effects without reaching levels necessary for a therapeutic action. On the other hand, over utilization may cause side effects or toxicity to a much greater extent than any possible benefit. Thus is critically important that a patient follow prescribed directions on medications, yet, frequently patients forget whether they have taken medication and either omit doses or repeat them.

This problem is particularly severe for elderly patients who are generally beset with multiple ailments requiring numerous drugs and directions. The fading memory and confusion that come with age further compound the problem. Oftentimes, elderly patients could well lead independent self-sufficient lives but for their inability to follow a therapeutic regimen necessary to their health and well-being. Caps of the "reminder" type will be an important adjunct in drug therapy as the number of elderly people increases and new potent drugs are utilized.

A considerable number of pill-timing schemes have been used to solve the problem of reminding a patient to take a dose of medicine or reminding him he has already taken that dose. The most used ones involve some scheme of compartmentalization of the necessary medication, such that the pills are placed in compartments labeled as to day, to dose number or time of day, or serially numbered. These devices are reasonably satisfactory if a responsible person is available and has the time and patience to fill the compartments properly.

In dispensing pills of a single type, a number of window-containing bottle caps have been invented. Through the window a movable element marked with an index is visible. In only a few devices does the indicating element index in position relative to the window each time the cap is loosened, removed, replaced, and re-tightened. Thus, by looking at the index mark displayed through the window, a user can see where in repetitive sequence of dose he or she is.

One of the most serious disadvantages of prior art devices of the window indexing type is that if the user does not turn the device far enough during the opening or closing process, the index will fail to advance properly, or fail to advance at all. These devices provide no indication that the index has failed to advance unless the user notices the index value before opening and then after closing, an unlikely event with most users, especially the elderly, who may not understand how the device operates. In addition, most prior art devices fail to provide positive locking in both directions of movement, thus, the index may be moved appropriately when the device is opened or closed, but additional movement is not prevented when the device is moved in the opposite direction thus allowing the index to drift, often causing failure, particularly after the device has been used over a period of time.

Specifically, the device of U.S. Pat. No. 4,011,829, issued Mar. 15, 1977 to Wachsmann et al., attempts to provide positive locking in both directions, but because of the direction of the tooth designed to prevent movement of the index upon closure, the device may not work reliably, particularly after wearing with use. Also, the device of Wachsmann does not provide space for the ratchet teeth to slide past the engagement teeth when the device is moving in a direction wherein such teeth should disengage, which may cause unreliable operation over a period of time. Another drawback of this device is its inclusion of the "child proofing" feature with the indexing feature, which makes the device more complex then necessary. Other features of this device, such as the method of providing the lost motion drive and the requirement of a post in the middle of the elements to hold the device together, also increase its complexity and cost of assembly.

The device of U.S. Pat. No. 3,151,599 issued Oct. 6, 1964 to Livingston provides positive locking in both directions, but it does so by means of very closely spaced projections that would be difficult to manufacture and assemble economically. Furthermore, this device does not provide space for the projections to move while sliding past each other when not engaged.

The device of U.S. Pat. No. 4,666,051 issued May 19, 1987 to Trick provides positive locking in both directions, but this device will work only with a bayonet type mount and requires that the bottom portion of the device be the container for the medication, therefore, the device is not suitable for separate attachment to an existing container cap. This device also does not provide an indication that is has worked properly.

Another disadvantage of these prior three art devices is that they cannot be distributed separately for attachment to a sealing cap of an existing bottle.

The device of European Patent 0 230 323, issued Jan. 24, 1986 to Schwab requires that the device be formed with a cavity in the top and bottom pieces. This device only provides a click when rotated in one direction, and does not provide positive locking of the indicator. Also, this device would appear to require close manufacturing tolerances and would be costly to assemble. Although the device would appear to be able to be attached to a separate sealing cap, the sealing cap would have to be of a particular dimension to mate with the cavity and cruciform projection, and therefore this device would be unable to be attached to a common, flat surfaced, sealing cap.

All the above prior art devices are designed to fit a specific cap or they are integrated into a particular bottle cap. None appear to be designed for installation on existing caps from various sources. In particular, none is designed to be installed on a cap having a flat upper surface, which is common for sealing caps in use today.

It is thus apparent that there is a need in the art for an improved indicator cap that provides positive controlled movement of the index on both opening and closing of the device, and that can be attached to an existing bottle cap, while also providing an indication to the user that the index has functioned properly each time the device is used.

SUMMARY OF THE INVENTION

It is an object of the present invention to provide an indicator cap for a medication dispensing bottle or the like that provides an indication each time the bottle is opened and then re-closed.

It is another object of this invention to provide a device that has positive control of the index member during both the opening and the closing motions.

Yet another object of the invention is to provide an audible sound when the device has been rotated sufficiently to move the index to the next location and to also provide an audible sound when the device has been rotated sufficiently to re-cock the device for the next open-close sequence.

Still another object is to provide space within the device for the locking mechanisms to slide past each other when not engaged to allow such mechanisms to work reliably over a long period of time.

Another object of the present invention is to combine functions usually requiring several components into single components to reduce the complexity of the device and provide ease of manufacturability.

A further object of the present invention is to provide an indicator cap that can be attached to the existing flat surface of the sealing cap of a medication dispensing bottle by the user of the medication.

A still further object of the present invention is to provide an indicator cap that can be attached to a flat surface larger or smaller than the diameter of the indicator cap, while still retaining its indicator functions by providing an indication of when it has worked properly.

These and other objects of the present invention are provided by means of an indicator cap having an outer cover shaped in the manner of a conventional bottle cap with a window in the top piece of the cap. Underneath the window, and within the body of the device, is an indicator wheel having numbers, days, times, etc. engraved or printed thereon which are visible through the window to indicate when a dose of the medication was or should be taken. The indicator wheel contains a pawl formed therein or attached thereto that engages a set of teeth formed in the underside of the top piece of the outer cover which engages the teeth only when the device is being opened. This engagement causes the indicator wheel to move to the next index location each time the cap is opened. Underneath the indicator wheel, and attached to the outer cover is a snap cover which contains a pawl formed therein or attached thereto. The pawl engages a set of teeth on the indicator wheel to prevent the indicator wheel from moving with respect to the ratchet when the device is being closed. The pawls on the two wheels, and the teeth formed opposite the pawls are designed such that the index wheel moves to a new location upon opening the cap, and is kept in that location when the cap is closed, allowing the window in the top piece to uncover the next indicator as the device is closed.

Both pawls are formed or attached such that space is provided for the pawl to move out of the way when being moved in a direction where the teeth are disengaged. The pawl moves away from the teeth as the teeth slide over the pawl, and as the pawl slides past the edge of a tooth, it makes an audible sound as it snaps back into place. Thus, the device makes a sound when it has been opened a sufficient amount for the index to move to the next location, and it also makes a sound when it has been closed sufficiently to re-cock the mechanism for the next cycle.

To provide for ease of assembly during the manufacturing process, the snap cover is provided with flexing legs that compress while the snap cover is being placed into the outer cover, and snap into a groove in the outer cover to firmly hold the device together and prevent disassembly.

An extension plug is provided to allow the indicator cap to be attached to a sealing cap that is larger in diameter than the indicator cap. The extension plug attaches to the snap cover and is long enough to extend out the bottom of the indicator cap to allow attachment of a large diameter sealing cap.

BRIEF DESCRIPTION OF THE DRAWINGS

The above and other objects, features, and advantages of the invention will be better understood by reading the following more particular description of the invention, presented in conjunction with the following drawings, wherein.

DESCRIPTION OF THE PREFERRED EMBODIMENT

The following description is of the best presently contemplated mode of carrying out the present invention. This description is not to be taken in a limiting sense but is made merely for the purpose of describing the general principles of the invention. The scope of the invention should be determined with reference to the appended claims.

The invention is primarily comprised of three parts: the outer cover, the indicator wheel, and the snap cover. In addition, the device uses adhesive tape or a similar method to affix the snap cover to the existing sealing cover of a medicine dispenser, bottle or the like. As a user opens the bottle the outer cover of the device is generally twisted in a counterclockwise direction looking down on the cap. The initial twisting motion does not turn the sealing cap to open the bottle, but instead, through a ratchet pawl and gear teeth, turns the indicator wheel to advance it to the next index location. Although the indicator wheel has advanced, the next index location is not yet visible in the window because the outer cover turned with the indicator wheel. When the outer cover reaches a predetermined angle with respect to the snap cover, and therefore the sealing cap of the bottle since the two are attached, the sealing cap begins to turn and eventually the two caps are removed from the bottle. The user then takes the prescribed dosage of medication and places the two caps back on the bottle. Then the user turns the caps clockwise to begin tightening the seal with the bottle. When the sealing cap reaches its limit and is tight, the outer cover continues to turn. A pawl on the snap cover meshes with teeth on the indicator wheel to hold the indicator wheel in place while the outer cover turns to expose the next index location through the window.

As the outer cover is loosened, the pawl on the snap cover slides over the teeth on the indicator wheel because it has room to flex away from these teeth. As the pawl passes over the next tooth, the spring action of the pawl snaps it over the edge of the tooth causing a snapping or clicking sound. Likewise as the cap is being closed, the pawl on the indicator wheel slides over the teeth on the outer cover and makes a click as it passes over the edge of a tooth. Therefore, a click is heard by the user when the indicator wheel has advanced to the next index location, and a second click is heard when closing the cap as the mechanism is re-cocked for the next cycle. Both pawls are designed with sufficient space behind them to allow them to move out of the way of the teeth, giving long term reliability, and they are designed to spring back into place after passing a tooth, which causes the audible sound that informs the user that the mechanism is working correctly.

Figure 1:
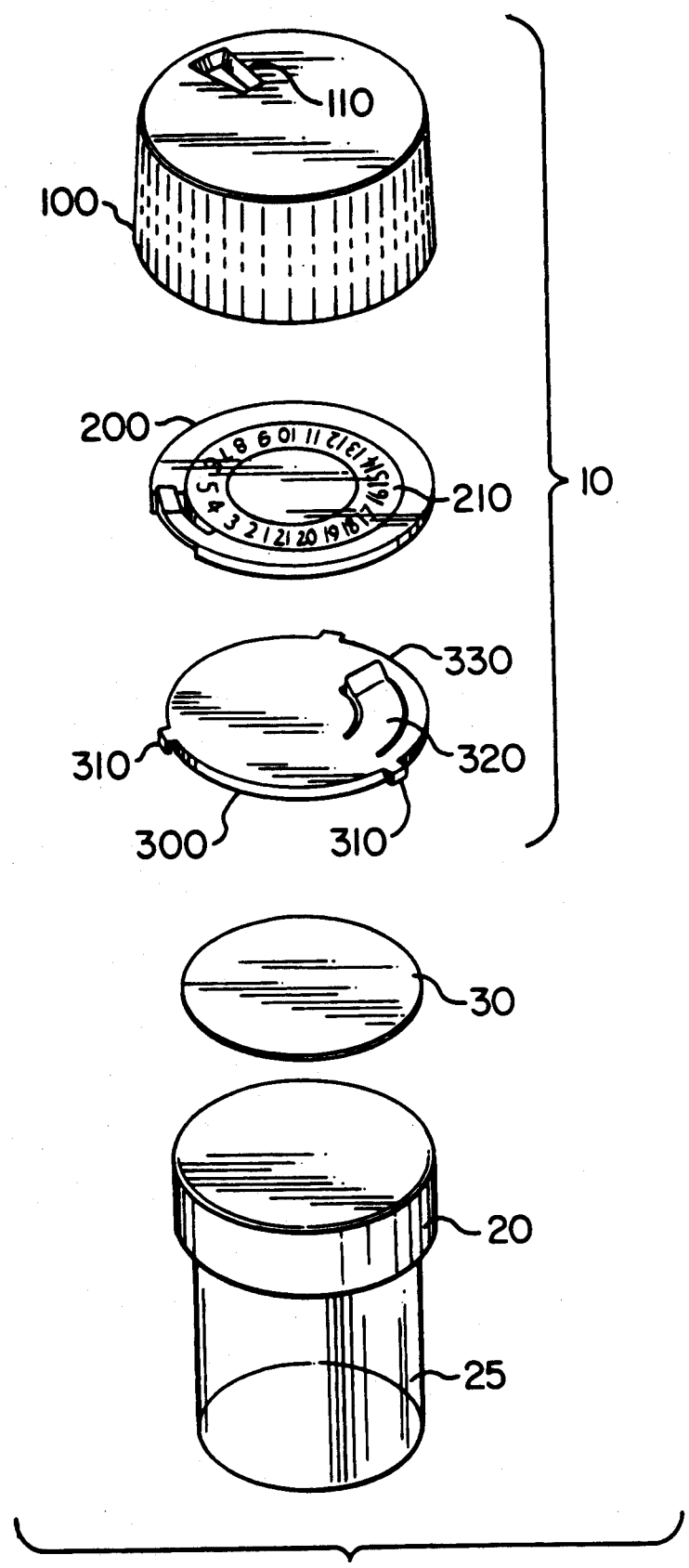
FIG. 1 shows an exploded perspective view of the invention as seen from the top.

Referring now to FIG. 1, a top perspective view of an indicator cap 10 is shown. The cap 10 is comprised of an outer cover 100 which fits over an indicator wheel 200. A snap cover 300 fits inside the outer cover 100 and is held into the outer cover 100 by projections 310. The indicator wheel 200 is contained between the snap cover 300 and the outer cover 100. The snap cover 300 is attached to the sealing cap 20 of a bottle 25 using adhesive tape 30. Other methods of attaching the snap cover 300 to the sealing cap 20 could be used, for example, a fitted cover could be formed on the bottom of the snap cover 300 that would slide over the sealing cap 20 to hold the indicator cap 10 in place over the sealing cap 20. As a user grasps the outside of the outer cover 100 to turn the cap, the rotary motion is transferred to the snap cover 300 through projections 310 and to the sealing cap 20 by the adhesive tape 30 to turn the sealing cap 20 and remove it from the bottle 25. The connection between the sealing cap 20 and the bottle 25 could be by means of threads, bayonet mount or other suitable connection including "child proof" cap connections. The indicator cap 10 is suitable for child proof caps, which generally require that the cap be pushed inward to remove it, because the inward motion of the outer cover 100 will be transferred to the snap cover 300 and thence to the sealing cap 20. A window 110 in the outer cover 100 is used to view index marks or digits 210 located on the indicator wheel 200. Window 110 is only wide enough for one of the digits 210 to be visible at any time.

Figure 1A:
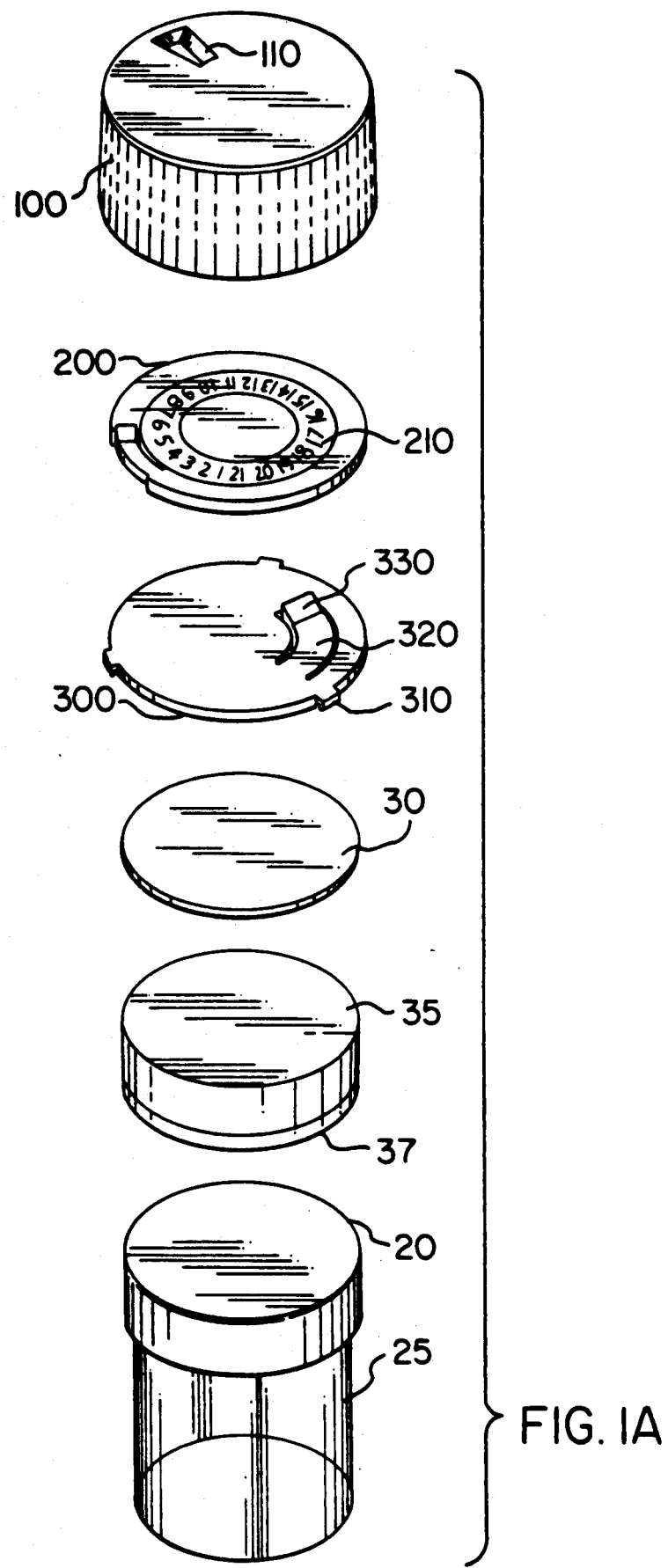
FIG. 1A shows an exploded perspective view of the invention as seen from the top, including a view of the extender plug.

By using the adhesive tape to attach the snap cover to the sealing cap, attachment will still work if the sealing cap is smaller than the snap cover. Therefore, the invention will attach to any sealing cap that will fit into the outer cover, even if the sealing cap is smaller than the outer cover. If the sealing cap is larger than the outer cover, attachment will be possible by using an extender plug, as shown in FIG. 1A. The extender plug 35 fits into the outer cover 100 and attaches to the snap cover 300 using the adhesive tape 30 as described above. The extender plug 37 is long enough to extend beyond the bottom of the outer cover. A second piece of adhesive tape 37 is used to attach the extender plug to the sealing cap. Since the bottom of the extender plug extends beyond the outer cover, it can be attached to a sealing cap that is of a larger diameter than the outer cover. The sealing cap is exposed when attachment occurs in this way, so the user could grasp the sealing cap to open the bottle, thus preventing the indicator from working properly, however, since the double click will not be heard when the cap is opened and closed in this manner, the user would know that the device had been used improperly. The outer cover is tall enough for the user to grasp it and open it in the proper manner, even when it is attached to a sealing cap with a large diameter.

Figure 2:
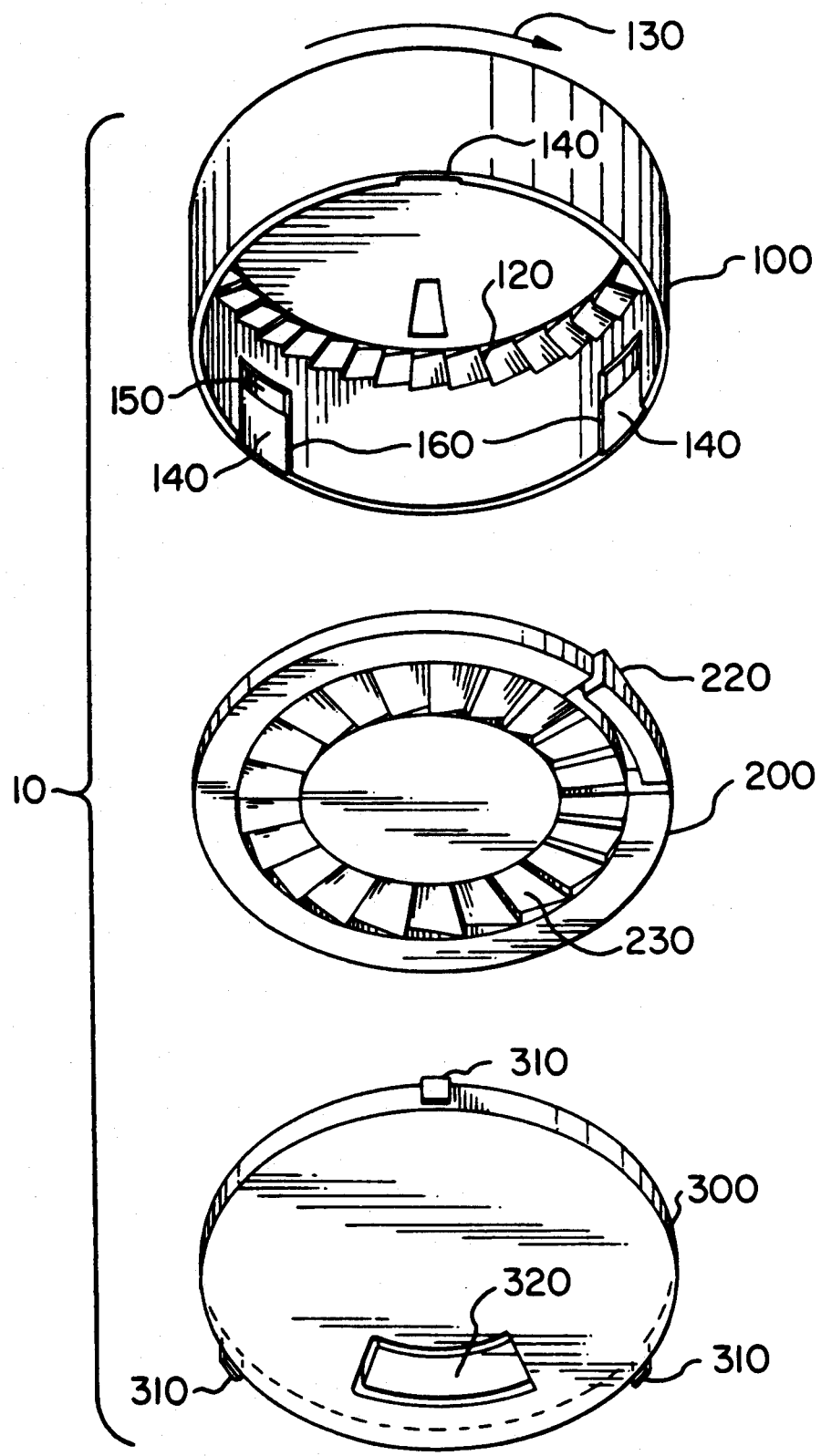
FIG. 2 shows an exploded perspective view of the three major elements of the invention as seen from the bottom.

FIG. 2 is a perspective view of the indicator cap 10 shown from the bottom to better illustrate the two ratchet systems employed in the device to achieve optimum operation. Gear teeth 120 are formed in the bottom side on the outer cover 100 in a manner that allows them to mesh with the pawl 220, located on the indicator wheel 200, when the outer cover 100 is rotated in the direction of arrow 130. Rotation in the direction of arrow 130 is counterclockwise to a user looking down on the cap, although it appears clockwise in this view looking upward. A counterclockwise rotation is the normal movement for removing a cap, and as the outer cover 100 is rotated this way, the pawl 220 engages the teeth 120 which causes the indicator wheel to rotate in the direction of arrow 130.

Projections 310 on the snap cover 300 are designed to fit into slots 140 on the outer cover 100 and lock into groove 150. Since the slot 140 and the groove 150 are wider than the projections 310, a lost motion drive is formed whereby outer cover 100 can turn through a predetermined number of degrees before projections 310 are encountered by the sidewalls 160 of slot 140. Once the projections 310 make contact with the sidewall 160 of the slot 140, the snap cover 300 will begin to turn which will then turn the sealing cap 20 (FIG. 1). The number of degrees the outer cover 100 is allowed to turn is determined by the width of slot 140, and would generally correspond with the number of degrees between the index marks or digits 210 (FIG. 1) on the indicator wheel 200. It is to be appreciated by those skilled in the art that any suitable method of forming a lost motion drive would enable the invention to function properly.

FIGS. 1 and 2 should be viewed together to best illustrate replacing the cap 10 on the bottle 25. When the indicator cap 10 is replaced on the bottle 25, the cap 10 is turned in a direction opposite arrow 130 (that is, clockwise as viewed from the top of the cap). Until the sealing cap 20 is tight on the bottle 25, sealing cap 20, snap cover 300 and outer cover 100 will turn in unison. Once the sealing cap 20 is tight on bottle 25, the sealing cap 20 will cease to turn, however, because of the lost motion drive formed by the projections 310 on the snap cover 300, the slots 140, and the grooves 150 in the outer cover 100, the outer cover 100 will continue to turn in the direction opposite arrow 130. Friction between the outer cover 100 and the indicator wheel 200 will attempt to turn the indicator wheel 200 along with the outer cover 100, however, the tooth 330 on the pawl 320 of the snap cover 300 will engage teeth 230 on the indicator wheel 200 to prevent the indicator wheel 200 from turning. Since the indicator wheel 200 was turned in the direction of arrow 130 when the cap was opened, and since the indicator wheel 200 is prevented from turning in the opposite direction upon closure, the index marks or digits 210 will advance one position in the window 110.

It is to be appreciated by those skilled in the art that the pawl and matching teeth of the two ratchets could be placed on either device. That is, both pawls could be located on the indicator wheel, or both sets of teeth could be located on the indicator wheel, and the device will work correctly. Also, other types of mechanisms that allow motion in only one direction could be used in place of the ratchet systems.

Figure 3:
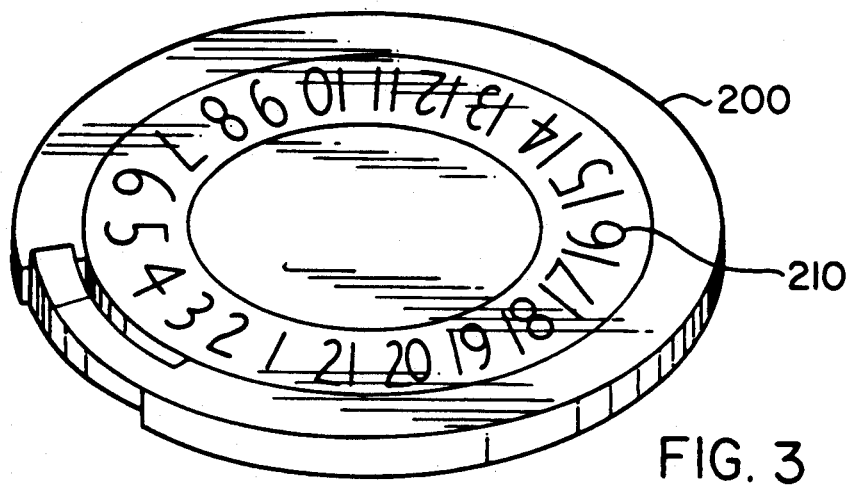
FIG. 3 shows a perspective view of the indicator wheel from the top illustrating a label affixed to the indicator wheel.

The number of index marks that can be placed on the indicator wheel 200 is determined by the width of slot 140 as well as the number of teeth 120 in the outer cover 100 and the number of teeth 230 in the indicator wheel 200. Because of the tolerance between the pawls and the teeth, the device can easily be made having indicators for different dosages. This tolerance also provides for ease of manufacturability. Of course, the width of the window 110 must correspond to the width of one index mark. FIG. 3 shows the indicator wheel 200 and better illustrates the index marks 210. Here the index marks consist of the digits 1 through 21 which might correspond to medication to be taken every day for three weeks. Other index marks could be used, for example, if medication were to be taken three times a day for seven days, the index marks might consist of the digits 1–7 each repeated three times with the letters M (morning), N (noon), and E (evening) placed over each repetition of numbers. The index marks may be molded into the indicator wheel 200 or printed on a label which is then attached to the indicator wheel 200.

Figure 4:
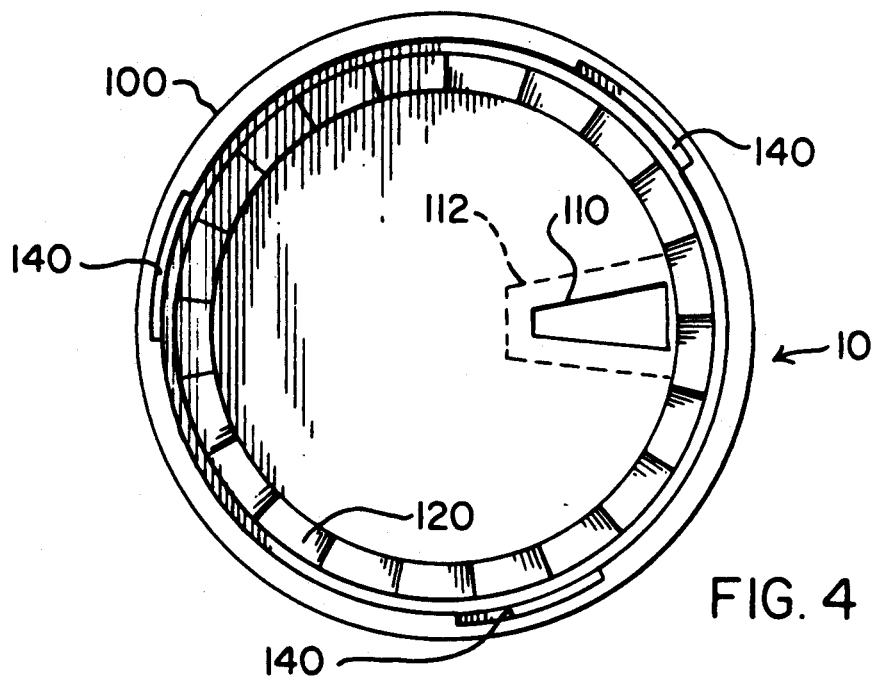
FIG. 4 shows a view of the outer cover from directly below.

Referring now to FIG. 4, a bottom view of the cap 10 is shown. Slots 140 are shown to be equally spaced from each other and window 110 is shown having a beveled edge 112, angled toward the outside of the outer cover 100. In this figure there are twenty one teeth 120, which corresponds to the 21 digits on the indicator wheel 200 (shown in FIG. 3).

Figure 5:
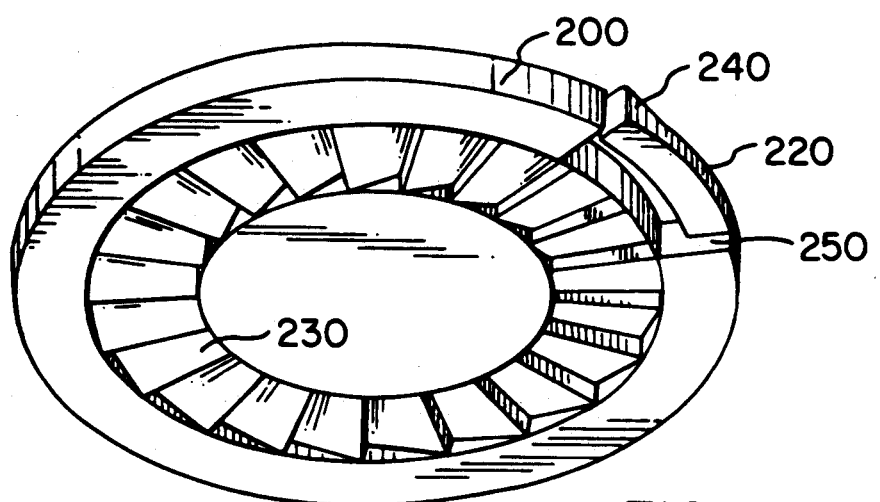
FIG. 5 shows a perspective view of the indicator wheel from the bottom.

FIG. 5 is a bottom perspective view of the indicator wheel 200, showing the teeth 230 and the pawl 220. A tooth 240 extends above the top surface of the indicator wheel 200 to engage the teeth 120 of the outer cover 100 (shown in FIG. 2). The pawl 220 is formed into the indicator wheel 200, however, the pawl 220 is not as thick as the indicator wheel, a space 250 being left below the pawl 220. This space 250 allows the tooth 240 of the pawl 220 to retract below the upper surface of the indicator wheel 200 when the teeth 120 of the outer cover 100 are moving in a direction which will not engage the tooth 240, that is, when the outer cover is moving in a direction opposite the arrow 130 of FIG. 2. This movement occurs when the cap is being tightened on the bottle. As the outer cover is tightened, one of the teeth 120 will depress the tooth 240 which will depress the pawl 220. By forming the indicator wheel 200 out of a resilient material, such as plastic, the pawl 220 will have a spring effect which will bias the pawl 220 and the tooth 240 toward the outer cover 100. As the trailing edge of one of the teeth 120 passes over the pawl, the pawl will spring back into place. This movement results in an audible snap or click which is loud enough to be heard by the person operating the cap. Thus the person knows that the mechanism has been re cocked for the next cycle.

Figure 6:
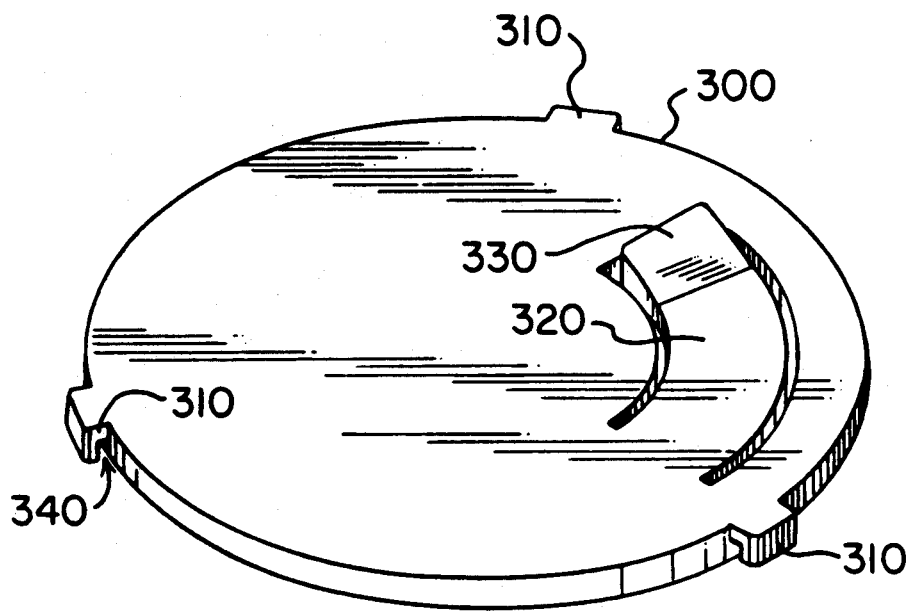
FIG. 6 shows a perspective view of the snap cover from the top.

FIG. 6 is a top perspective view of the snap cover 300, showing a pawl 320 having a tooth 330. The tooth 330 is designed to engage the teeth 230 of the indicator wheel 200 (FIG. 5) when the cap is being closed. This engagement prevents the indicator wheel 200 from moving with respect to the snap cover 300, which allows the outer cover 100 to move the window 110 over the next index mark. When the cap is being opened, the teeth 230 of the indicator wheel 200 and the tooth 330 of the snap cover 300 are not engaged and function in a manner similar to the teeth 120 of the outer cover 100 and the pawl 220 of the indicator wheel. That is, the pawl 320 is formed in such a way that space is left below the pawl so that one of the teeth 230 can depress the pawl 320 when the cap is being opened. As the trailing edge of one of the teeth 230 passes over the tooth 330, the pawl 320 springs back to its normal position causing a audible snap or click which can be heard by the person opening the cap. This snap or click alerts the user that the indicator wheel has advanced to the next index mark.

Thus the combination of the pawl 320 and the teeth 230 as well as the pawl 220 and teeth 120 give the user an audible indication that the indicator wheel has advanced one index mark on opening, and that the mechanism has been re-cocked for the next cycle when the cap is closed.

The projections 310 are designed to pass through the slot 140 of the outer cover 100 (FIG. 2) and lock into grooves 150. Furthermore, the projections 310 are designed with space 340 that allows the projections 310 to compress as they are being inserted into the outer cover 100 during assembly. When the projections 310 are inserted far enough into slots 140 to reach the grooves 150, the projections expand and snap into the grooves 150 to lock the snap cover 300 in place. Because of this arrangement, the cap 10 is easy to assemble and does not easily come apart.

Figure 7:
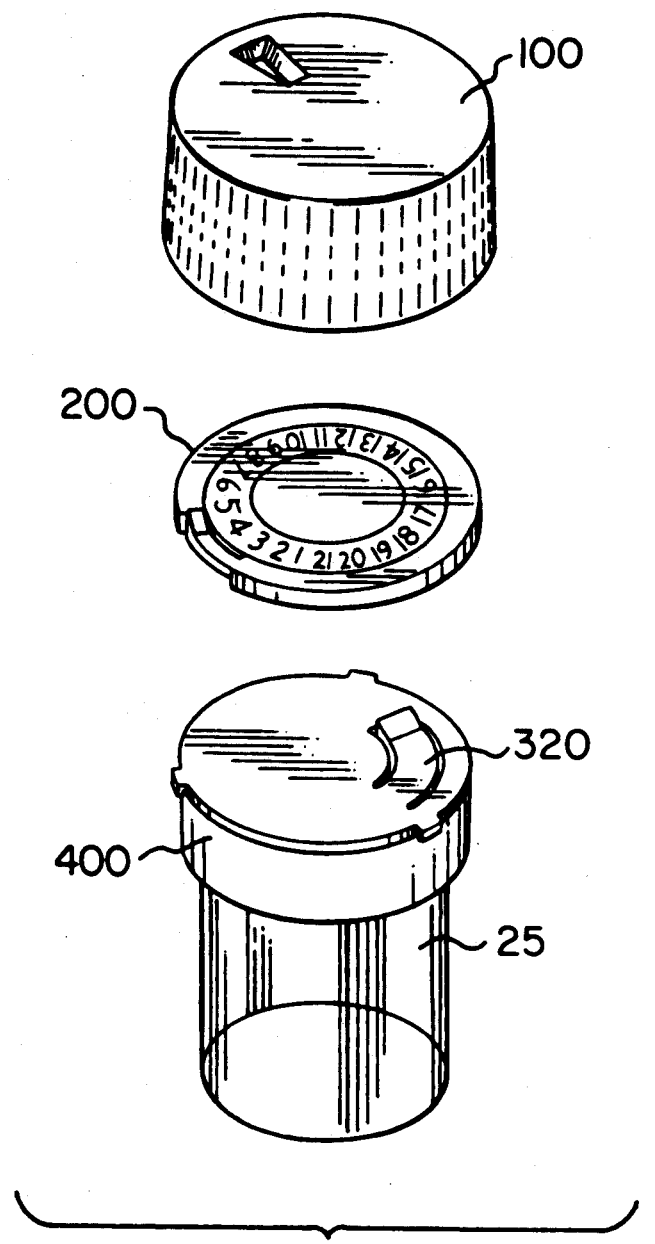
FIG. 7 shows an alternative embodiment of the device wherein the snap cover is molded with the sealing cap.

FIG. 7 shows an alternative embodiment of the indicator cap. While the first embodiment, as shown in FIGS. 1–6, is intended to be purchased separately from the medicine dispenser and attached by the user, this alternative embodiment would be included with the medicine dispenser. The outer cover 100 and the indicator wheel 200 remain unchanged in this embodiment, however, the snap cover and the sealing cap have been combined into a new ratchet cap 400. Since the pawl 320 is formed into the snap cover, this embodiment must leave room under the pawl 320 for the pawl to flex when the cap is being opened. Also, the ratchet cap must have an inner seal (not shown) which prevents the medicine from entering the indicator cap mechanism, and to prevent dirt or other contaminants from moving between the indicator cap mechanism and the bottle 25. Because of the method of constructing child proof caps, such a seal is normally present in such caps.

Figure 8:
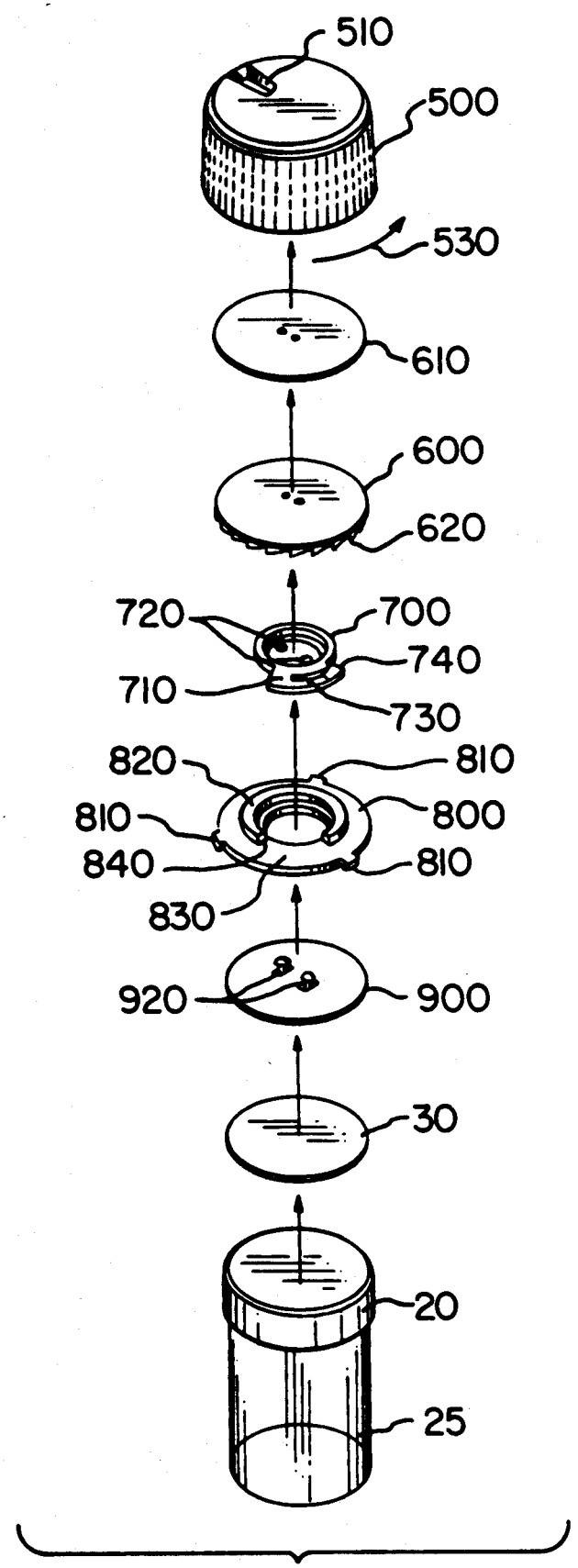
FIG. 8 shows a second alternative embodiment of the invention.

FIG. 8 shows a second alternative embodiment of the indicator cap. The outer cover 500 has a window 510 and fits over the entire mechanism. A gear wheel 600 has a label 610 attached to it. As an alternative, the index marks that would be contained on the label 610 could be molded into the gear wheel 600. A retainer disc 800 having projections 810 is connected to the outer cover 500 by having the projections 810 fit into slots (not shown) in the outer cover 500. The slots in the outer cover 500, although similar to the slots 140 in the outer cover 100 of the first embodiment, are only as wide as necessary for the projections 810 to fit. Therefore the slots in the outer cover 500 and the projections 810 do not form a lost motion drive. Located between the retainer disc 800 and the gear wheel 600 is a ratchet 700. A bottom plate 900 is attached to the ratchet 700 with two split arrowhead projections 920 that fit into holes 720 of the ratchet 700. The bottom plate 900 is attached to the sealing cap with adhesive tape 30. An arm 710 on the ratchet 700 fits through a slot 830 in a flange 820 on the retainer disc 800. This arm 710 and the slot 830 form a lost motion drive.

In operation, outer cover 500 is turned in the direction of arrow 530 to open the cap. Since retainer disc 800 is attached to outer cover 500, retainer disc 800 also turns in the direction of arrow 530. Friction between the outer cover 500 and the gear wheel 600 cause the gear wheel 600 to also move in the direction of arrow 530, causing one of the teeth 620 in the gear wheel 600 to move past the ratchet tooth 740, and causing the gear wheel to move the distance of one indicator mark on the label 610. When an edge 840 of the retainer disc 800 contacts the arm 710 of the ratchet 700, the ratchet 700 begins to move and the teeth 620 no longer move past the ratchet tooth 740. Once the ratchet 700 starts moving the bottom plate 900 moves and the sealing cap 20 moves to open the container.

Upon closure, all the components move together, because of friction, until the sealing cap 20 forms a seal on the bottle 25. Once the seal is formed, the sealing cap 20 ceases to move, which stops the movement of the bottom plate 900 and the ratchet 700. The outer cover 500 and the retainer disc 800 continue to move until the arm 710 of the ratchet 700 contact one edge 840 of the flange 820. This last movement brings the next index mark on the label 610 into view of the window 510.

Figure 9:
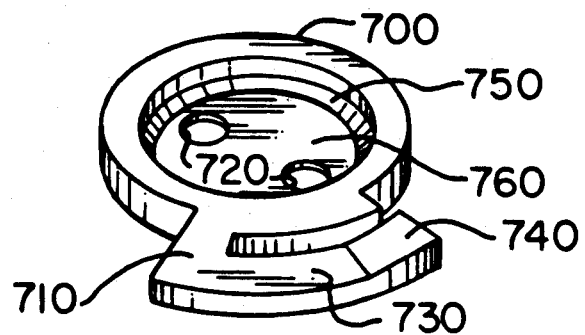
FIG. 9 shows the ratchet of the second alternative embodiment.

FIG. 9 shows a top perspective view of the ratchet 700, illustrating the mounting holes 720, the arm 710, the pawl 730, and the ratchet tooth 740. Also shown is a rim 750 of a well 760 which is used to center the ratchet 700 on the retainer disc 800.

Figure 10:
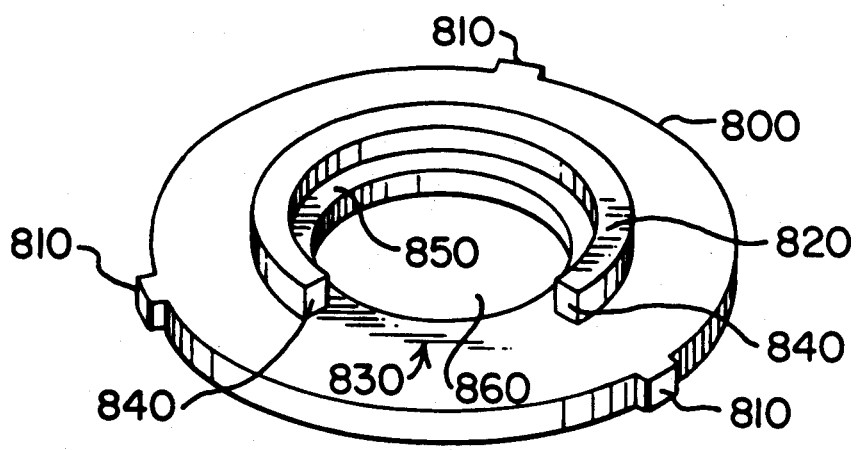
FIG. 10 shows the retainer disc of the second alternative embodiment.

FIG. 10 shows a top perspective view of the retainer disc 800 and illustrates the projections 810, the flange 820 including the gap 830, and the flange edges 840. Also shown is a rim 850 onto which the rim 750 of the latch 700 is centered. The well 760 of the latch 700 extends downward through the bore 860 of the retainer disc 800 so that the arrowhead projections 920 of the base plate 900 can pass through the holes 720 in the ratchet 700.

Figure 11:
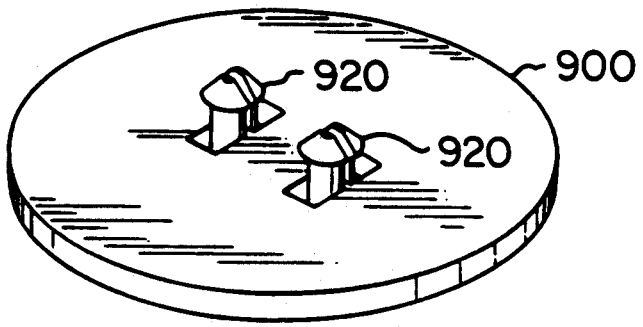
FIG. 11 shows the bottom plate of the second alternative embodiment.

FIG. 11 is a top perspective view of the bottom plate 900 and illustrates the split arrowhead projections 920 which are used to attach the base plate 900 to the ratchet 700.

While the invention herein disclosed has been described by means of specific embodiments and applications thereof, numerous modifications and variations could be made thereto by those skilled in the art without departing from the spirit and scope of the present invention. It is therefore to be understood that within the scope of the appended claims, the invention may be practiced otherwise than as specifically described herein.

What is claimed is:

1. An indicator cap for attachment to a sealing cap of a container, said sealing cap being a pre-existing container cap that forms a seal on said container, and for indicating the number of times said container has been opened comprising:

(a) an outer cover comprising a top piece, an indicator window located in said top piece, and a skirt attached to an outer circumference of said top piece and extending away from said top piece;
(b) a snap cover lacking means for directing securing said indicator cap to said container and having means for attaching said snap cover to an inner surface of said skirt that allows said skirt to rotate a predetermined number of degrees in each direction without causing rotation of said snap cover while rotation of said skirt beyond said predetermined number of degrees will cause said snap cover to rotate;
(c) an indicator wheel disposed between said snap cover and said top piece having indicating means on a surface facing said indicator window;
(d) rotation means connecting said indicator wheel and said outer cover for causing movement of said indicator wheel only when said outer cover is rotated in a first direction; and
(e) antirotation means connecting said snap cover and said indicator wheel for preventing movement of said indicator wheel when said snap cover is rotated in a second direction opposite said first direction;
(f) means for attaching said snap cover to said sealing cap of said container.

2. An indicator cap as defined in claim 1 wherein said rotation means connecting said indicator wheel and said outer cover comprises:

(a) a pawl attached to said indicator wheel having a tooth facing an inner surface of said top piece;
(b) means for spring biasing said pawl toward said top piece, and teeth located on an inner surface of said top piece arranged for engagement with said pawl only when said outer cover is rotated in said first direction.

3. An indicator cap as defined in claim 1 wherein said antirotation means connecting said snap cover and said indicator wheel comprises:

(a) a pawl attached to said snap cover having a tooth facing said indicator wheel;
(b) means for spring biasing said pawl toward said indicator wheel; and
(c) teeth located on a surface of said indicator wheel opposite said snap cover and arranged for engagement with said pawl only when said snap cover is rotated in said second direction.

4. An indicator cap as defined in claim 2 further including an opening to allow said pawl to be displaced away from said top piece a sufficient distance to allow said teeth on said top piece to pass over said pawl when said outer cover is rotated in said first direction.

5. An indicator cap as defined in claim 3 further including an opening to allow said pawl to be displaced away from said indicator wheel a sufficient distance to allow said teeth on said indicator wheel to pass over said pawl when said snap cover is rotated in said second direction.

6. An indicator cap as defined in claim 1 further including means for producing an audible sound when said outer cover rotates near the end of said predetermined number of degrees in each direction.

7. An indicator cap as defined in claim 1 wherein said means for attaching said snap cover further includes flexing means attached to said snap cover to allow said snap cover to be installed in a groove in said skirt while preventing said snap cover from being removed from said groove after installation.

8. An indicator cap as defined in claim 1 further comprising:
   (a) extension means located between said snap cover and said means for attaching said snap cover to said sealing cap, said extension means being sufficiently long to extend beyond an edge of said skirt; and
   (b) means for attaching said extension means to said sealing cap whereby said indicator cap may be attached to a sealing cap that has a diameter larger than an inside diameter of said skirt.

9. An indicator cap as defined in claim 1 wherein the means for attaching said snap cover to said sealing cap comprises adhesive means for adhering said snap cover to said sealing cap.

10. An indicator cap as defined in claim 9 wherein said adhesive means comprises a double-sited adhesive pad.

* * * * *